US012649013B2

(12) United States Patent
Wu

(10) Patent No.: US 12,649,013 B2
(45) Date of Patent: Jun. 9, 2026

(54) FRAGRANCE DIFFUSER WITH MAGNETIC COMPONENT

(71) Applicant: Blueprint Technology CO., LTD., Taipei City (TW)

(72) Inventor: Hua Ting Wu, Taipei City (TW)

(73) Assignee: Blueprint Technology Co., LTD., Taipei City (TW)

( * ) Notice: Subject to any disclaimer, the term of this patent is extended or adjusted under 35 U.S.C. 154(b) by 301 days.

(21) Appl. No.: 18/474,035

(22) Filed: Sep. 25, 2023

(65) Prior Publication Data

US 2024/0374774 A1 Nov. 14, 2024

(30) Foreign Application Priority Data

May 12, 2023 (TW) ................................. 112204724

(51) Int. Cl.
*A61L 9/12* (2006.01)

(52) U.S. Cl.
CPC ..................................... *A61L 9/12* (2013.01)

(58) Field of Classification Search
CPC ........ A61L 9/04; A61L 9/12; A61L 2209/133; A61L 2209/15
USPC ........ 239/34, 36, 44, 45, 46, 47, 48, 49, 50, 239/51, 52, 53, 54, 55, 56, 57, 58, 59
See application file for complete search history.

(56) References Cited

U.S. PATENT DOCUMENTS

| 6,254,248 B1 * | 7/2001 | McAuley | ............ | A01M 1/2083 |
| | | | | 362/255 |
| 10,081,309 B2 * | 9/2018 | Gao | ........................ | B60R 11/02 |
| 11,796,126 B2 * | 10/2023 | Chao | ........................ | F16B 1/00 |

* cited by examiner

Primary Examiner — Devon C Kramer
Assistant Examiner — Sean V Meiller
(74) Attorney, Agent, or Firm — Best & Flanagan LLP

(57) ABSTRACT

The invention provides a fragrance diffuser with a magnetic component. The fragrance diffuser with the magnetic component is disposed on a smartphone with a wireless charging element, comprising a bottom cover, a magnetic unit, a fragrance unit, and a top cover. The bottom cover has a first surface and a second surface opposite to the first surface. The first surface has a first accommodation groove. The second surface has a second accommodation groove and at least one slot penetrating the first surface and the second surface. The second accommodation groove is disposed surrounding the at least one slot. The magnetic unit is disposed in the first accommodation groove of the bottom cover. The fragrance unit is disposed in the second accommodation groove and exposed in the at least one slot. The top cover is disposed on the fragrance unit and connected to the bottom cover.

7 Claims, 8 Drawing Sheets

117

11A

FRAGRANCE DIFFUSER WITH MAGNETIC COMPONENT

CROSS-REFERENCE TO RELATED APPLICATION(S)

This application claims the priority benefit of TW application serial No. 112204724 filed on May 12, 2023, the entirety of which is hereby incorporated by reference herein and made a part of the specification.

BACKGROUND OF THE INVENTION

1. Field of the Invention

The present invention relates to a fragrance diffuser, in particular to a fragrance diffuser with a magnetic component disposed on a smartphone.

2. Description of the Related Art

A smartphone is an electronic device widely used and carried by a user. When the user operates the smartphone for a long time, the user may be in a weary mental condition. To solve the problem, the user can utilize a fragrance diffuser to reinvigorate. However, since the fragrance diffuser is usually disposed on a table and is not portable, the user cannot constantly use the fragrance diffuser to keep up their spirits when they leave the environment that has the fragrance diffuser.

In addition, the smartphone is widely used by the user, in particular to a smartphone with a wireless charging element. When the smartphone with the wireless charging element is charging wirelessly, the smartphone is disposed on a wireless charging board to be charged.

In other words, the wireless charging element is enabled when the smartphone is disposed on the wireless charging board to be charged. However, when the smartphone with the wireless charging element is not charging, the wireless charging element is disabled. Consequently, when the function of the wireless charging element can be further enhanced, the utilization of the smartphone can be further raised.

Accordingly, how to provide a fragrance diffuser with a magnetic component to solve the problems mentioned above is an urgent subject to tackle.

SUMMARY OF THE INVENTION

In view of this, the invention provides a fragrance diffuser with a magnetic component. The fragrance diffuser with the magnetic component is disposed on a smartphone with a wireless charging element, comprising a bottom cover, a magnetic unit, a fragrance unit, and a top cover. The bottom cover has a first surface and a second surface opposite to the first surface. The first surface has a first accommodation groove. The second surface has a second accommodation groove and at least one slot penetrating the first surface and the second surface. The second accommodation groove is disposed around the at least one slot. The magnetic unit is disposed in the first accommodation groove of the first surface of the bottom cover. The fragrance unit is disposed in the second accommodation groove and exposed in the at least one slot. The top cover is disposed on the fragrance unit and connected to the bottom cover. The fragrance diffuser with the magnetic component of the present invention is capable of diffusing fragrance to stimulate spirit of a user.

As mentioned above, the present invention facilitates the user to conveniently, easily, and promptly dispose the fragrance diffuser with the magnetic component on the smartphone with a wireless charging element. Furthermore, the fragrance diffuser with the magnetic component is capable of diffusing various fragrances to stimulate spirit of the user. In addition, the present invention provides the advantages of low cost, fragrant scents, and lasting effects.

DETAILED DESCRIPTION OF THE INVENTION

Figure 1:
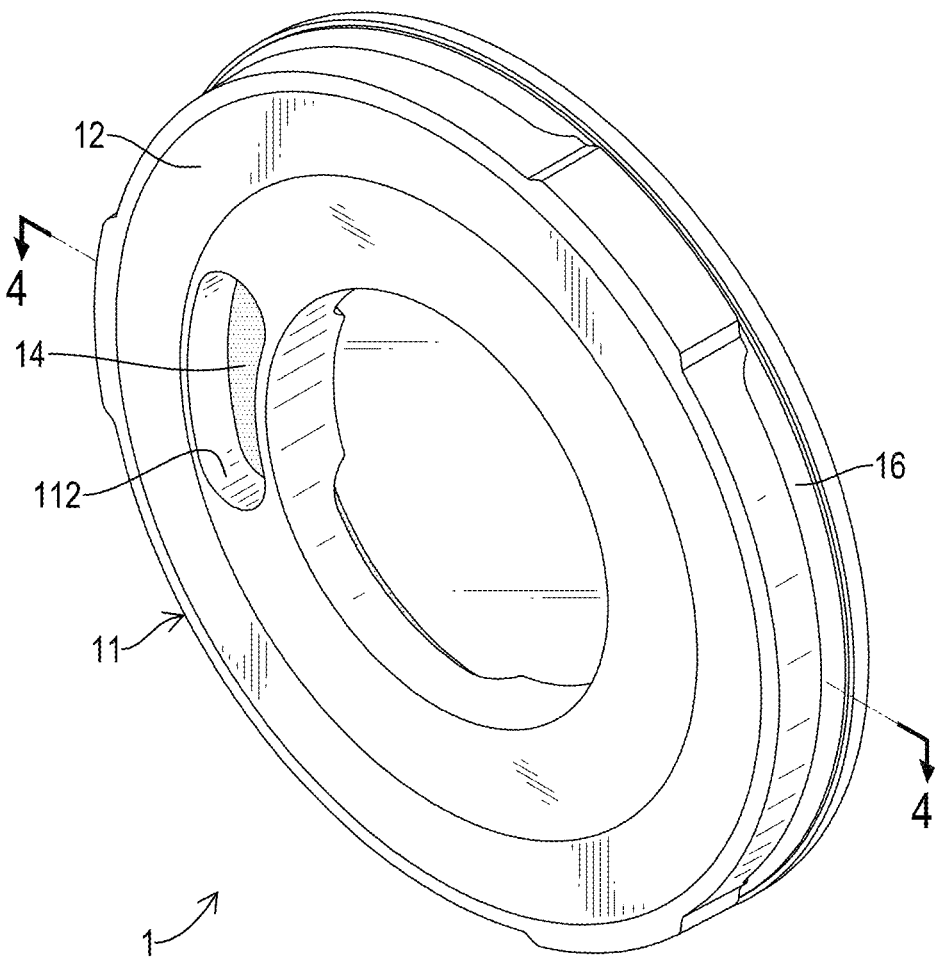
FIG. 1 is a stereo diagram of the fragrance diffuser with the magnetic component in the present invention.
Figure 2:
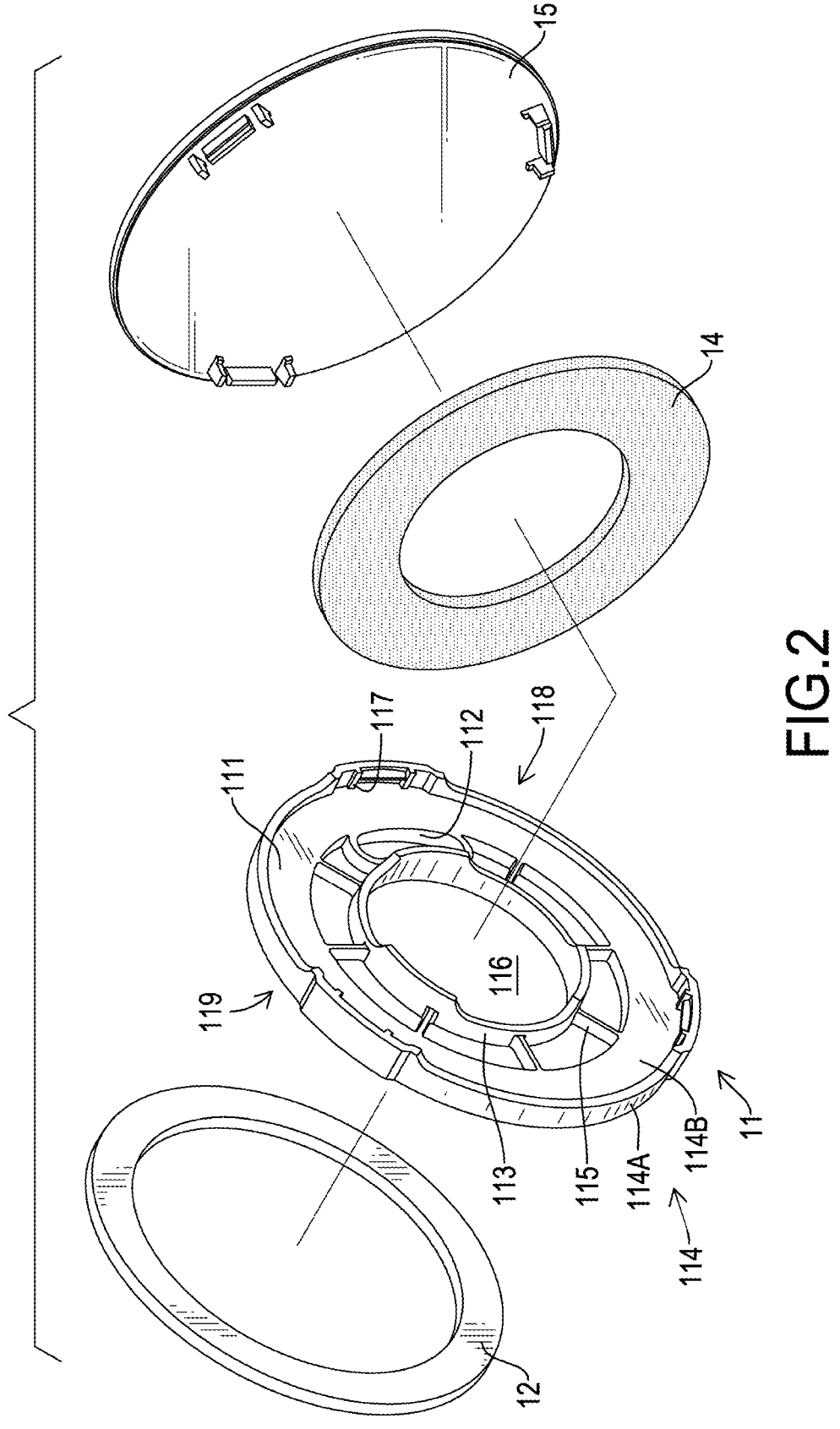
FIG. 2 is an exploded view of the fragrance diffuser with the magnetic component in the present invention.
Figure 3:
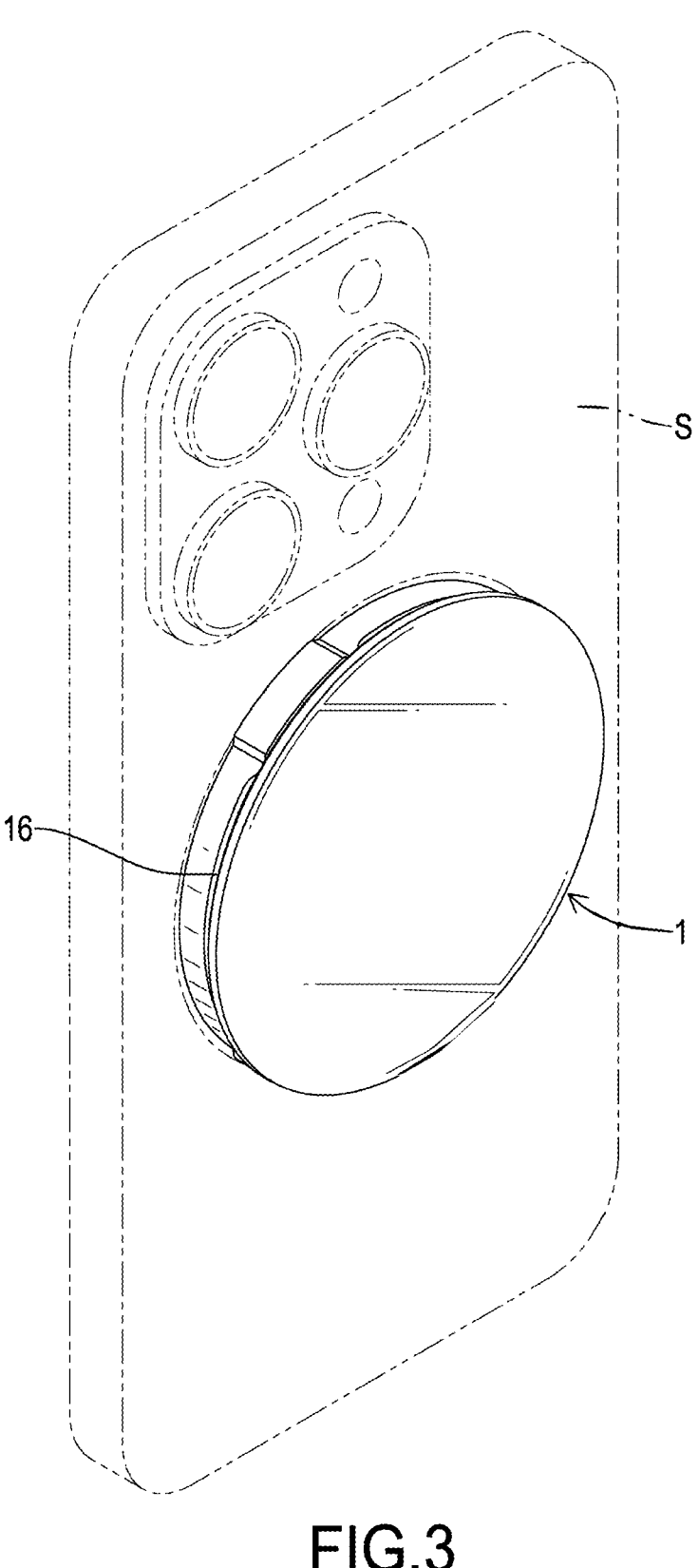
FIG. 3 is a usage state schematic diagram of the fragrance diffuser with the magnetic component in the present invention.

Refer to FIG. 1 to FIG. 3. FIG. 1 is the stereo diagram of the fragrance diffuser with the magnetic component of the present invention. FIG. 2 is the exploded view of the fragrance diffuser with the magnetic component in the present invention. FIG. 3 is the usage state schematic diagram of the fragrance diffuser with the magnetic component in the present invention. The fragrance diffuser with the magnetic component 1 is disposed on a smartphone S with a wireless charging element. The fragrance diffuser with the magnetic component 1 comprises a bottom cover 11, a magnetic unit 12, a fragrance unit 14, and a top cover 15. The bottom cover 11 has a first surface 118 and a second surface 119 opposite to the first surface. The first surface 118 is disposed on the back of the smartphone S. The first surface 118 has a first accommodation groove 110. The second surface 119 has a second accommodation groove 111 and at least one slot 112 penetrating the first surface 118 and the second surface 119. The second accommodation groove 111 is disposed around the at least one slot 112. The magnetic unit 12 is disposed in the first accommodation groove 110 of the bottom cover 11. The fragrance unit 14 is disposed in the second accommodation groove 111 and exposed in the at least one slot 112. The top cover 15 is covered on the fragrance unit 14 and connected to the bottom cover 11.

In an embodiment of the present invention, the fragrance unit 14 comprises materials of paper, bamboo, cane, gypsum, ceramic, diatomaceous earth, wood, fabric, lava, or crystal. As shown in FIG. 1, since the fragrance unit 14 protrudes to the second accommodation groove 111, is mounted in the second accommodation groove 111, covers the opening 112 from the second surface 119 of the bottom cover 11, and is exposed out from the first surface 118 of the bottom cover 11 through the at least one slot 112, a user drops essential oils on the fragrance unit 14 through the at least one slot 112.

Figure 4:
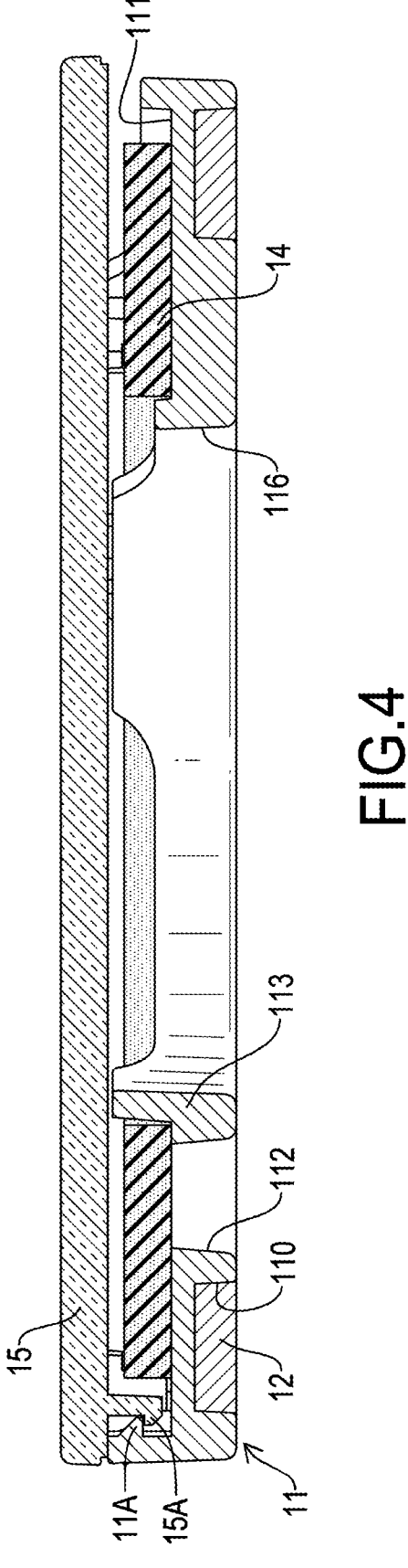
FIG. 4 is a cross sectional view of the top cover being connected to the bottom cover of the fragrance diffuser with the magnetic component in the present invention.

Refer to FIG. 4. FIG. 4 is the cross-sectional view of the top cover being connected to the bottom cover of the fragrance diffuser with the magnetic component in the present invention. In the embodiment of the present invention, the top cover 15 and the bottom cover 11 comprise various connection methods. For instance, the top cover 15 is connected to the bottom cover 11 by hot melting. Alternatively, the top cover 15 is connected to the bottom cover 11 by a mortise and tenon but is not limited thereto. The top cover 15 and the bottom cover 11 each respectively have a first engagement part 15A and a second engagement part 11A. The first engagement part 15A and the second engagement part 11A are respectively disposed at a side wall of the top cover 15 and at a side wall of the bottom cover 11. Taking the mortise and tenon as an example in FIG. 4, the first engagement part 15A and the second engagement part 11A are engaged with each other and are connected to the top cover 15 and the bottom cover 11.

Figure 5A:
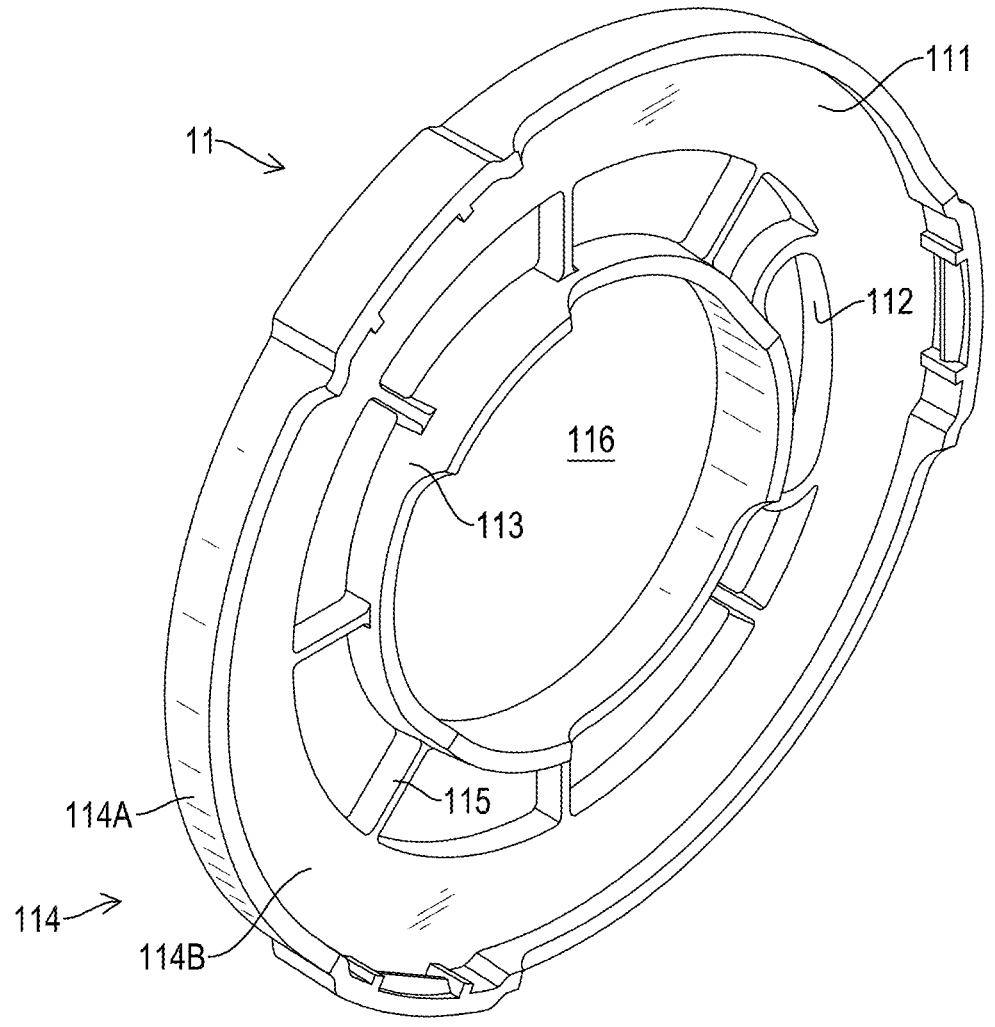
FIG. 5A and FIG. 5B are a stereo diagram and a schematic diagram of partial enlargement of the bottom cover of the fragrance diffuser with the magnetic component in the present invention.
Figure 5B:
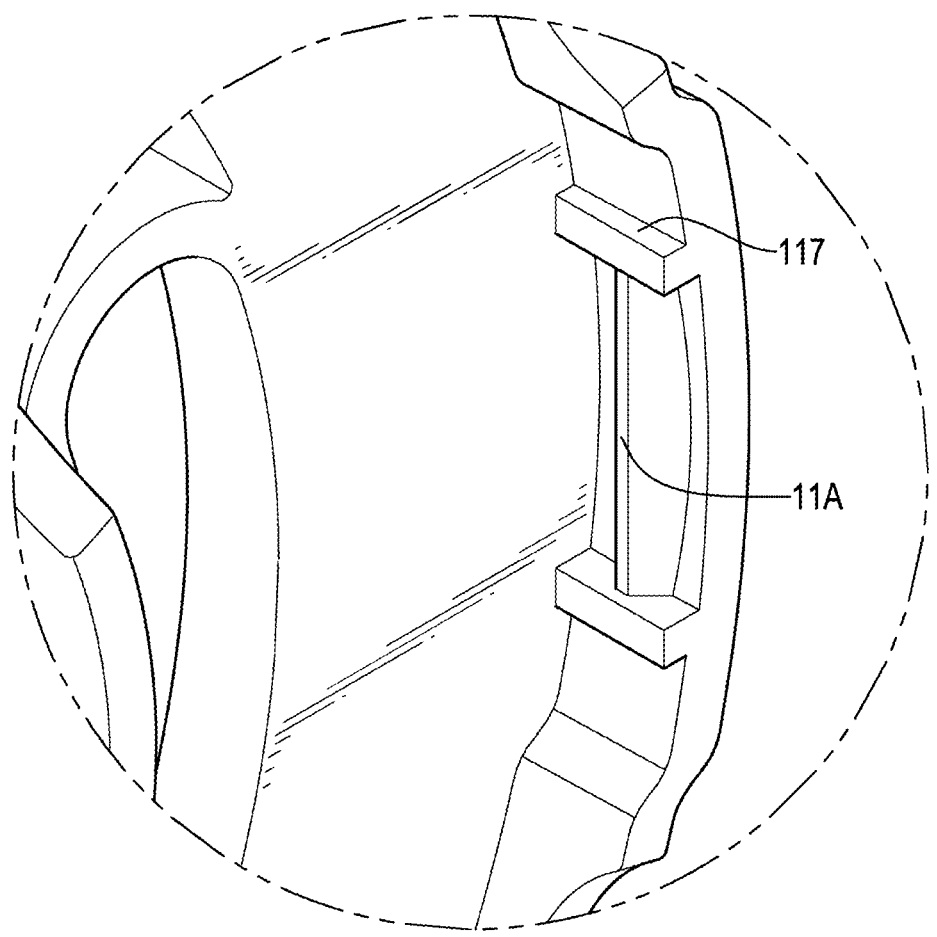

Refer to FIG. 5A and FIG. 5B. FIG. 5A and FIG. 5B are the stereo diagram and the schematic diagram of partial enlargement of the bottom cover of the fragrance diffuser with the magnetic component in the present invention. The bottom cover 11 of the fragrance diffuser with the magnetic component 1 is an annular bottom cover. The bottom cover 11 comprises a first annular part 113, a second annular part 114, and a connection part 115. The first annular part 113 has a via hole 116. The via hole 116 penetrates the first surface and the second surface of the bottom cover 11. The second annular part 114 is disposed surrounding the first annular part 113. The second annular part 114 has a wall surface 114A and a bottom surface 114B. The wall surface 114A is perpendicularly connected to the bottom surface 114B. The second accommodation groove 111 is disposed at the bottom surface 114B of the second annular part 114. A plurality of connection parts 115 are respectively disposed between an outer edge of the first annular part 113 and the bottom surface 114B of the second annular part 114 to connect to the first annular part 113 and the second annular part 114. As shown in FIG. 1, FIG. 3, and FIG. 5A, at least one vent 16 is concaved from an edge of the wall surface of the second annular part and formed between the bottom cover 11 and the top cover 15. The fragrance unit 14 is further exposed in the at least one vent 16. Therefore, the at least one vent 16 facilitates the fragrance unit 14 to emit scent. At least one slot 112 is formed between the outer edge of the first annular part 113 and the inner edge of the second annular part 114 by the connection part 115. The at least one slot 112 is disposed at an annular interval. Moreover, the at least one slot 112 is disposed surrounding the via hole 116, that is, the via hole 116 is disposed relative to the at least one slot 112. For example, the via hole 116 is disposed at a center of the at least one slot 112. In addition, in FIG. 5B, the bottom cover 11 further comprises two protrusions 117. The two protrusions 117 are respectively disposed at two sides of the second engagement part 11A. By this way, when the second engagement part 11A is engaged with the first engagement part 15A, the bond strength between the top cover 15 and the bottom cover 11 can be enhanced by the two protrusions 117.

Figure 6A:
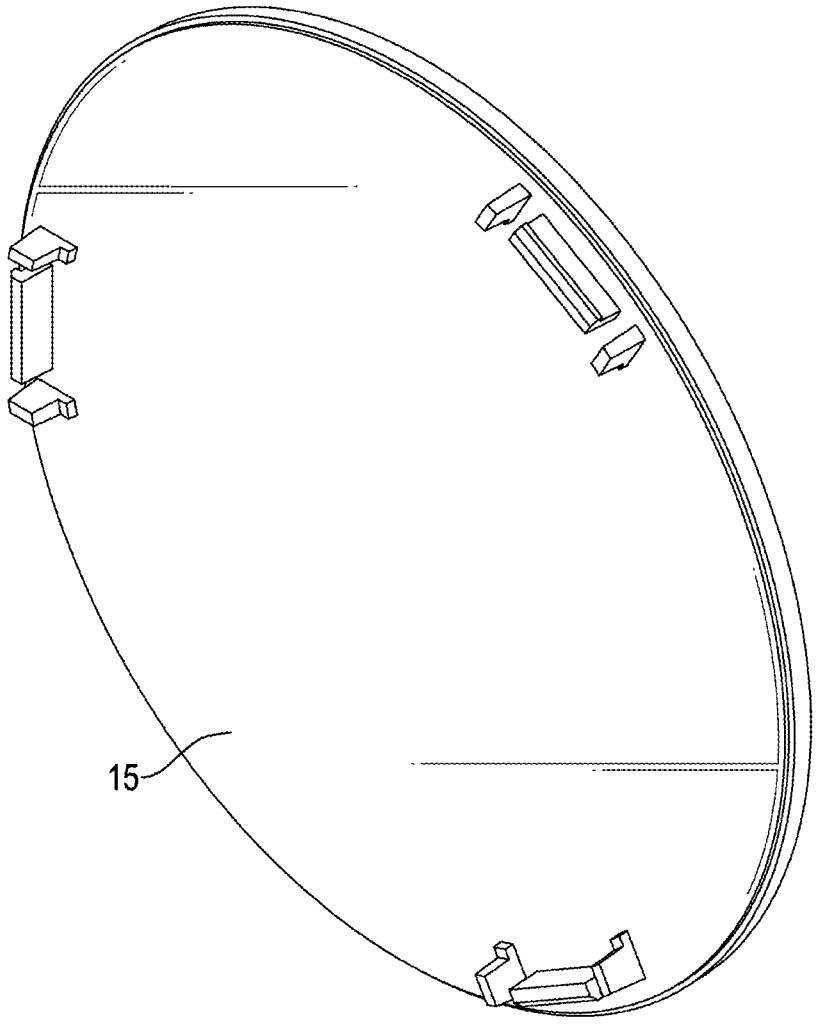
FIG. 6A and FIG. 6B are a stereo diagram and a schematic diagram of partial enlargement of the top cover of the fragrance diffuser with the magnetic component in the present invention.
Figure 6B:
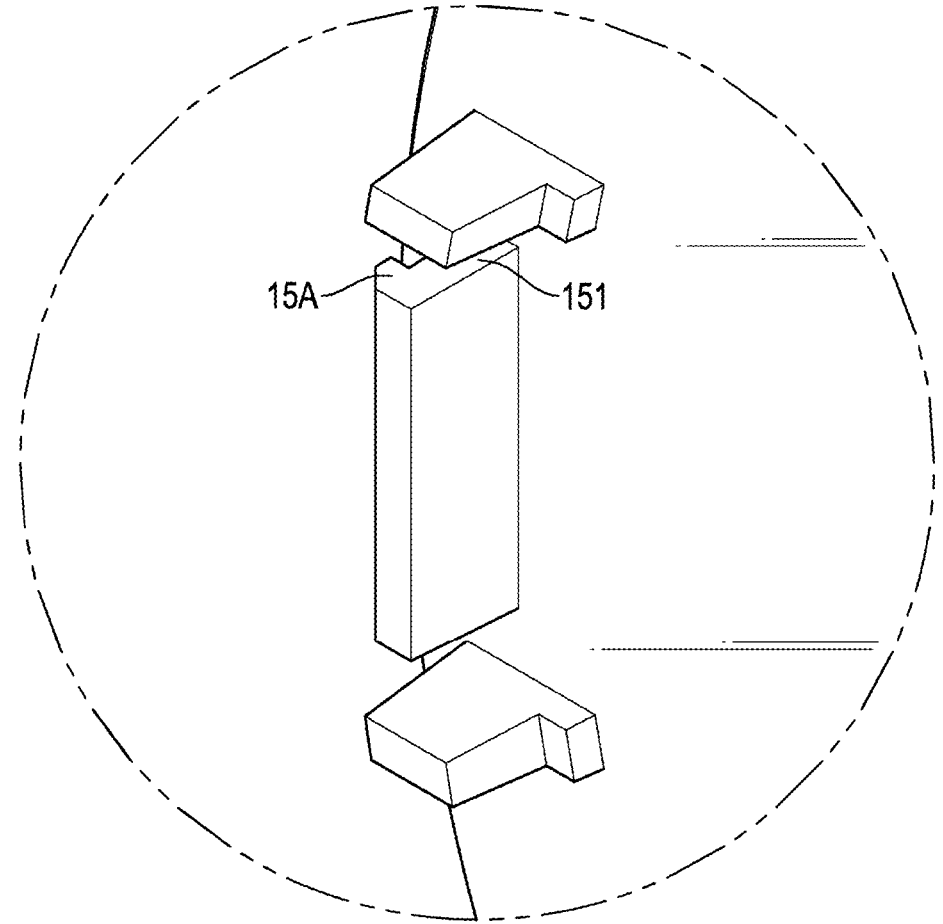

Refer to FIG. 6A and FIG. 6B. FIG. 6A and FIG. 6B are the stereo diagram and the schematic diagram of partial enlargement of the top cover of the fragrance diffuser with the magnetic component in the present invention. In FIG. 6, the top cover 15 further comprises two trenches 151. The two trenches 151 are respectively disposed at two sides of the first engagement part 15A. The two trenches 151 are engaged with the two protrusions 117 in FIG. 5B. By this way, when the second engagement part 11A is engaged with the first engagement part 15A, the bond strength between the top cover 15 and the bottom cover 11 can be enhanced by the two trenches 151.

The fragrance diffuser with the magnetic component 1 is disposed on the smartphone S with a wireless charging element such as iPhone® series of Apple incorporation. A logo of Apple incorporation is disposed on a backside of the smartphone S of iPhone® series. Hence, the top cover 15 utilizes a transparent material for preventing the fragrance diffuser with the magnetic component 1 disposed on the smartphone from covering the logo. Moreover, the via hole 116 is disposed corresponding to a position of the logo on the backside of the smartphone S for exposing the logo when the user uses the fragrance diffuser with the magnetic component 1 to diffuse fragrance. Alternatively, in another embodiment, the top cover 15 is in an annular shape corresponding to a shape and a position of the via hole 116 of the bottom cover 11 for exposing the logo of iPhone®.

In summary, the present invention facilitates the user to conveniently, easily, and promptly dispose the fragrance diffuser with the magnetic component on the smartphone with a wireless charging element. Furthermore, the fragrance diffuser with the magnetic component is capable of diffusing various fragrances to stimulate spirit of the user. In addition, the present invention provides the advantages of low cost, fragrant scents, and lasting effects.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:

1. A fragrance diffuser with a magnetic component, disposed on a smartphone with a wireless charging element, and comprising:
   a bottom cover, having a first surface and a second surface opposite to the first surface; wherein the first surface has a first accommodation groove, the second surface has a second accommodation groove, at least one slot penetrates the first surface and the second surface, and the second accommodation groove is disposed surrounding the at least one slot;
   the magnetic component disposed in the first accommodation groove of the bottom cover, surrounding the at least one slot;
   a fragrance unit, disposed in the second accommodation groove and exposed in the at least one slot;
   a top cover, disposed on the fragrance unit and connected to the bottom cover;
   wherein the bottom cover is an annular bottom cover, comprising:
   a first annular part, having a via hole; wherein the via hole penetrates the first surface and the second surface of the bottom cover;
   a second annular part, disposed surrounding the first annular part, having a wall surface and a planar surface; wherein the wall surface is perpendicularly connected to the planar surface, and the second accommodation groove is disposed at the planar surface of the second annular part; and a plurality of connection parts, respectively disposed between an outer edge of the first annular part and an inner edge of the second annular part, connected to the first annular part and the second annular part, and forming the at least one slot between the outer edge of the first annular part and the planar surface of the second annular part; and at least one vent, concaved from an edge of the wall surface of the second annular part, and between the bottom cover and the top cover;

wherein the fragrance unit is further exposed in the at least one vent.

2. The fragrance diffuser with the magnetic component as claimed in claim 1, wherein the top cover and the bottom cover each respectively have a first engagement part and a second engagement part, the first engagement part is disposed at a side wall of the top cover, the second engagement part is disposed at a side wall of the bottom cover, and the first engagement part and the second engagement part are engaged with each other.

3. The fragrance diffuser with the magnetic component as claimed in claim 2, wherein the top cover further comprises two trenches, the bottom cover further comprises two protrusions, the two protrusions are respectively disposed at two sides of the second engagement part, the two trenches are respectively disposed at two sides of the first engagement part, and the two protrusions are engaged in the two trenches.

4. The fragrance diffuser with the magnetic component as claimed in claim 1, wherein the top cover is connected to the bottom cover by hot melting.

5. The fragrance diffuser with the magnetic component as claimed in claim 1, wherein the fragrance unit comprises materials of paper, bamboo, cane, gypsum, ceramic, diatomaceous earth, wood, fabric, lava or crystal.

6. The fragrance diffuser with the magnetic component as claimed in claim 1, wherein the top cover is made of a transparent material.

7. The fragrance diffuser with the magnetic component as claimed in claim 6, wherein the via hole is disposed corresponding to a pattern at a backside of the smartphone.

* * * * *